United States Patent
Ahner et al.

(10) Patent No.: US 9,217,714 B2
(45) Date of Patent: *Dec. 22, 2015

(54) REFLECTIVE SURFACES FOR SURFACE FEATURES OF AN ARTICLE

(71) Applicant: Seagate Technology LLC, Cupertino, CA (US)

(72) Inventors: Joachim W. Ahner, Livermore, CA (US); David M. Tung, Livermore, CA (US); Stephen Keith McLaurin, Sunnyvale, CA (US); Travis W. Grodt, Fremont, CA (US)

(73) Assignee: Seagate Technology LLC, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/029,700

(22) Filed: Sep. 17, 2013

(65) Prior Publication Data
US 2014/0160481 A1 Jun. 12, 2014

Related U.S. Application Data

(60) Provisional application No. 61/734,247, filed on Dec. 6, 2012.

(51) Int. Cl.
G01N 21/95 (2006.01)

(52) U.S. Cl.
CPC ............ *G01N 21/95* (2013.01); *G01N 21/9506* (2013.01)

(58) Field of Classification Search
USPC ............. 356/301, 601–604; 250/237 G, 226, 250/225, 559.23, 559.27
See application file for complete search history.

(56) References Cited

U.S. PATENT DOCUMENTS

| | | | |
|---|---|---|---|
| 4,207,467 A | * | 6/1980 | Doyle ..................... 250/338.1 |
| 4,477,890 A | | 10/1984 | Ceshkovsky et al. |
| 4,551,919 A | | 11/1985 | Sakata et al. |
| 4,598,997 A | | 7/1986 | Auderset et al. |
| 4,618,773 A | * | 10/1986 | Drukier ................... 250/363.02 |
| 4,794,550 A | | 12/1988 | Greivenkamp |
| 4,806,776 A | | 2/1989 | Kley |
| 4,975,571 A | * | 12/1990 | McMurtry et al. ........ 250/231.16 |
| 5,058,178 A | | 10/1991 | Ray |
| 5,066,130 A | * | 11/1991 | Tsukiji et al. ................ 356/494 |
| 5,131,755 A | | 7/1992 | Chadwick et al. |

(Continued)

FOREIGN PATENT DOCUMENTS

| | | |
|---|---|---|
| JP | 06-241758 A | 9/1994 |
| JP | 08-075661 A | 3/1996 |

(Continued)

OTHER PUBLICATIONS

Candela CS10, Optical X-BeamTM Surface Analyzer, Product Description (www.klatencor.com/defect-inspection/candela-cs10.html), accessed Apr. 17, 2013.

(Continued)

*Primary Examiner* — Sang Nguyen (57) ABSTRACT

Provided herein is an apparatus, including a photon emitter configured for emitting photons onto a surface of an article; a first reflective surface and a second reflective surface configured to reflect the photons onto the surface of the article; and a processing means configured for processing signals from a photon detector array corresponding to photons scattered from surface features of the article.

20 Claims, 6 Drawing Sheets

(56) References Cited

U.S. PATENT DOCUMENTS

| | | | |
|---|---|---|---|
| 5,168,322 A | 12/1992 | Clarke et al. | |
| 5,455,870 A | 10/1995 | Sepai et al. | |
| 5,610,392 A * | 3/1997 | Nagayama et al. | 250/226 |
| 5,627,638 A | 5/1997 | Vokhmin | |
| 5,661,559 A | 8/1997 | Brezoczky et al. | |
| 5,726,455 A | 3/1998 | Vurens | |
| 5,737,072 A | 4/1998 | Emery et al. | |
| 5,774,212 A | 6/1998 | Corby, Jr. | |
| 5,778,039 A | 7/1998 | Hossain et al. | |
| 5,781,649 A | 7/1998 | Brezoczky | |
| 5,859,698 A | 1/1999 | Chau et al. | |
| 5,898,491 A | 4/1999 | Horai et al. | |
| 5,933,236 A * | 8/1999 | Sommargren | 356/513 |
| 5,973,839 A | 10/1999 | Dorsel | |
| 6,256,097 B1 * | 7/2001 | Wagner | 356/369 |
| 6,392,745 B1 | 5/2002 | Mavliev et al. | |
| 6,449,036 B1 | 9/2002 | Wollmann et al. | |
| 6,476,908 B1 | 11/2002 | Watson | |
| 6,483,584 B1 * | 11/2002 | Lee et al. | 356/369 |
| 6,509,966 B2 | 1/2003 | Ishiguro | |
| 6,515,742 B1 | 2/2003 | Ruprecht | |
| 6,529,270 B1 | 3/2003 | Bills | |
| 6,542,248 B1 | 4/2003 | Schwarz | |
| 6,556,783 B1 | 4/2003 | Gelphman | |
| 6,559,458 B2 | 5/2003 | Rinn | |
| 6,559,926 B2 | 5/2003 | Yamaguchi et al. | |
| 6,617,087 B1 | 9/2003 | Rangarajan et al. | |
| 6,617,603 B2 | 9/2003 | Ishiguro et al. | |
| 6,809,809 B2 | 10/2004 | Kinney et al. | |
| 6,819,423 B2 * | 11/2004 | Stehle et al. | 356/369 |
| 6,822,734 B1 | 11/2004 | Eidelman et al. | |
| 6,847,907 B1 | 1/2005 | Novotny | |
| 7,207,862 B2 | 4/2007 | Nabeya et al. | |
| 7,433,031 B2 | 10/2008 | Xu et al. | |
| 7,474,410 B2 | 1/2009 | Moon | |
| 7,489,399 B1 * | 2/2009 | Lee | 356/369 |
| 7,684,057 B2 | 3/2010 | Sakai | |
| 7,751,609 B1 | 7/2010 | Berman | |
| 7,777,876 B2 | 8/2010 | Horai et al. | |
| 7,969,567 B2 | 6/2011 | Yoshida et al. | |
| 8,018,585 B2 | 9/2011 | Hariyama | |
| 8,077,305 B2 | 12/2011 | Owen et al. | |
| 8,139,232 B2 | 3/2012 | Wolf et al. | |
| 8,223,326 B2 * | 7/2012 | Kim et al. | 356/237.1 |
| 8,294,890 B2 | 10/2012 | Usuda | |
| 8,547,545 B2 | 10/2013 | Sasazawa et al. | |
| 2001/0036588 A1 | 11/2001 | Buschbeck et al. | |
| 2002/0088952 A1 | 7/2002 | Rao et al. | |
| 2004/0207836 A1 | 10/2004 | Chhibber et al. | |
| 2004/0231177 A1 | 11/2004 | Mies | |
| 2005/0067740 A1 | 3/2005 | Haubensak | |
| 2005/0099204 A1 | 5/2005 | Uh et al. | |
| 2005/0174575 A1 | 8/2005 | Norton et al. | |
| 2005/0280808 A1 | 12/2005 | Backhauss et al. | |
| 2006/0126062 A1 * | 6/2006 | Tuschel | 356/301 |
| 2006/0147814 A1 | 7/2006 | Liang | |
| 2006/0181700 A1 | 8/2006 | Andrews et al. | |
| 2007/0229852 A1 | 10/2007 | Wack et al. | |
| 2008/0174771 A1 | 7/2008 | Yan et al. | |
| 2008/0191137 A1 | 8/2008 | Poteet et al. | |
| 2008/0309927 A1 | 12/2008 | Grueneberg | |
| 2009/0009753 A1 | 1/2009 | Horai et al. | |
| 2009/0122304 A1 | 5/2009 | Jin et al. | |
| 2009/0320051 A1 | 12/2009 | Meerwald et al. | |
| 2009/0323051 A1 | 12/2009 | Matsui | |
| 2010/0053602 A1 | 3/2010 | Hayashi et al. | |
| 2010/0053603 A1 | 3/2010 | Sakaguchi et al. | |
| 2010/0091272 A1 | 4/2010 | Asada et al. | |
| 2011/0066382 A1 | 3/2011 | Adams | |
| 2011/0141272 A1 | 6/2011 | Uto et al. | |
| 2012/0140211 A1 | 6/2012 | Oshima et al. | |
| 2012/0194808 A1 | 8/2012 | Oka et al. | |
| 2013/0077159 A1 | 3/2013 | Tani et al. | |
| 2013/0198697 A1 | 8/2013 | Hotzel et al. | |
| 2013/0301040 A1 * | 11/2013 | Ahner et al. | 356/237.2 |
| 2014/0043621 A1 | 2/2014 | Ahner et al. | |
| 2014/0098364 A1 | 4/2014 | Ahner et al. | |
| 2014/0098368 A1 | 4/2014 | Ahner et al. | |
| 2014/0104604 A1 | 4/2014 | Ahner et al. | |
| 2014/0129179 A1 | 5/2014 | Xu et al | |
| 2014/0354980 A1 | 12/2014 | Tung et al. | |
| 2014/0354981 A1 | 12/2014 | Ahner et al. | |
| 2014/0354982 A1 | 12/2014 | Ahner et al. | |
| 2014/0354984 A1 | 12/2014 | Tung et al. | |
| 2014/0354994 A1 | 12/2014 | Ahner et al. | |

FOREIGN PATENT DOCUMENTS

| | | |
|---|---|---|
| JP | 08-178867 A | 7/1996 |
| JP | 2003-202214 | 7/2003 |
| JP | 3692685 B2 | 9/2005 |
| JP | 2006-308511 A | 11/2009 |
| JP | 2011-163872 A | 8/2011 |
| JP | 2012-026862 A | 2/2012 |
| JP | 2012-185121 A | 9/2012 |
| KR | 10-0763942 B1 | 10/2007 |
| KR | 10-0769342 B1 | 10/2007 |
| KR | 10-2011-021304 A | 3/2011 |
| WO | 96-05503 A1 | 2/1996 |

OTHER PUBLICATIONS

Candela CS20, Advanced Inspection for Compound Semiconductor and Optoelectronic Materials, Optical Surface Analyzer, KLA-TENCOR Corporation, 2010.

High-sensitivity, High-speed Dark-field Wafer-defect Inspection System-IS3000, Hitachi Review vol. 55, No. 2, pp. 73-77, Hitachi Ltd., 2006.

Hitachi High-Technologies I-5320/I-6300—Electron Beam Wafer Inspection System, (www.etesters.com/listing/ea101bfb-1422-08df-aaae-08c275a8ee86/1-5320_~_I-6300_-_Electron_Beam_Wafer_Inspection_System), accessed Jun. 19, 2013.

Hitachi High-Technologies IS3000—Dark Field Wafer Defect Inspection System, (www.etesters.com/listing/ea1312b5-1422-08df-aa4b-5fea5982b63b/IS3000_-_Dark_Field_Wafer_Defect_Inspection_System), accessed Jun. 19, 2013.

Hitachi High-Technologies LS6800—Wafer Surface Inspection System, (www.etesters.com/listing/ea1133d4-1422-08df-aad9-258baeaf6c16/LS6800_-_Wafer_Surfce_Inspection_System), accessed Jun. 19, 2103.

LS Unpatterned Wafer Inspection System, (hitachi-htc.ca/products/semiconductor-metrology-equipment/inspections-systems/wafer-inspection-system/ls-unpatterne), accessed Jun. 19, 2013.

* cited by examiner

REFLECTIVE SURFACES FOR SURFACE FEATURES OF AN ARTICLE

CROSS REFERENCE

This application claims the benefit of U.S. Provisional Patent Application No. 61/734,247, filed Dec. 6, 2012.

BACKGROUND

An article fabricated on a production line may be inspected for certain features, including defects that might degrade the performance of the article or a system comprising the article. For example, a hard disk for a hard disk drive may be fabricated on a production line and inspected for certain surface features, including surface and subsurface defects that might degrade the performance of the disk or the hard disk drive. Accordingly, apparatuses and methods may be used to inspect articles for features such as defects.

SUMMARY

Provided herein is an apparatus, including a photon emitter configured for emitting photons onto a surface of an article; a first reflective surface and a second reflective surface configured to reflect the photons onto the surface of the article; and a processing means configured for processing signals from a photon detector array corresponding to photons scattered from surface features of the article.

These and other features and aspects of the concepts presented herein may be better understood with reference to the following drawings, description, and appended claims.

DESCRIPTION

Before some particular embodiments are described in greater detail, it should be understood by persons having ordinary skill in the art that the particular embodiments described and/or illustrated herein do not limit the concepts presented herein, as elements in such particular embodiments may vary. It should likewise be understood that a particular embodiment described and/or illustrated herein has elements which may be readily separated from the particular embodiment and optionally combined with any of several other embodiments or substituted for elements in any of several other embodiments described herein.

It should also be understood by persons having ordinary skill in the art that the terminology used herein is for the purpose of describing some particular embodiments, and the terminology does not limit the concepts presented herein. Unless indicated otherwise, ordinal numbers (e.g., first, second, third, etc.) are used to distinguish or identify different elements or steps in a group of elements or steps, and do not supply a serial or numerical limitation. For example, "first," "second," and "third" elements or steps of embodiments need not necessarily appear in that order, and embodiments need not necessarily be limited to the three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art.

An article fabricated on a production line may be inspected for certain features, including defects that might degrade the performance of the article or a system comprising the article. For example, a hard disk for a hard disk drive may be fabricated on a production line and inspected for certain surface features, including surface and subsurface defects that might degrade the performance of the disk or the hard disk drive. Provided herein are apparatuses and methods for inspecting articles to detect and/or map certain surface features such as surface and/or subsurface defects. Embodiments of the invention will now be described in greater detail.

With respect to articles that may be inspected with apparatuses and methods herein, such articles include any article of manufacture or a workpiece thereof in any stage of manufacture having one or more surfaces (e.g., one or more optically smooth surfaces), examples of which include, but are not limited to, semiconductor wafers, magnetic recording media (e.g., hard disks for hard disk drives), and workpieces thereof in any stage of manufacture, including transparent articles such as glass blanks for magnetic recording media. Such articles may be inspected for certain surface features, including surface and/or subsurface defects that might degrade the performance of the article, which surface and/or subsurface defects include particle and stain contamination, as well as defects including scratches and voids. With respect to particle contamination, for example, particles trapped on a surface of an intermediate hard disk (i.e., workpiece) for a hard disk drive may damage subsequently sputtered films. Particle contamination may also contaminate a finished surface of a hard disk drive, leading to scratch formation, debris generation, and corruption of the spacing between the hard disk and the read-write head. As such, it is important to inspect articles with apparatus and methods herein to correct manufacturing trends leading to surface and/or subsurface defects and to increase product quality.

Figure 1A:
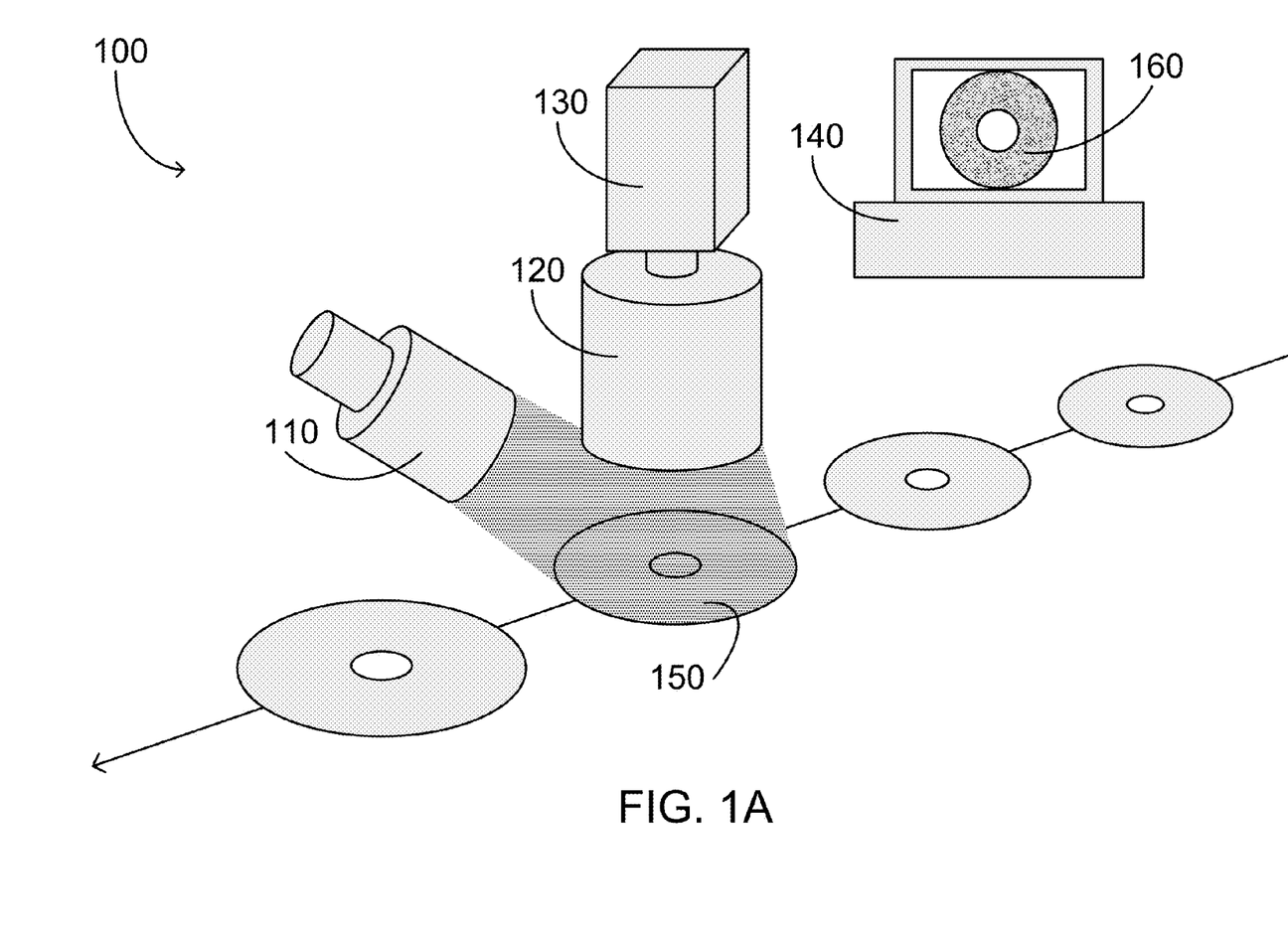
FIG. 1A provides a schematic illustrating detection of surface features of articles in accordance with an embodiment.

FIG. 1A provides a schematic for detecting and/or mapping surface features of articles, illustrating an apparatus 100 comprising a photon emitter 110, an optical setup comprising optical component 120, a photon detector array 130, and a computer or equivalent device 140, as well as an article 150 and a surface features map 160 of a surface of the article 150 in accordance with an embodiment; however, the articles and apparatuses of the invention, as well as methods of the invention, are not limited to the embodiments in FIG. 1A, as additional embodiments of the invention may be realized by the features described in more detail herein.

Figure 1B:
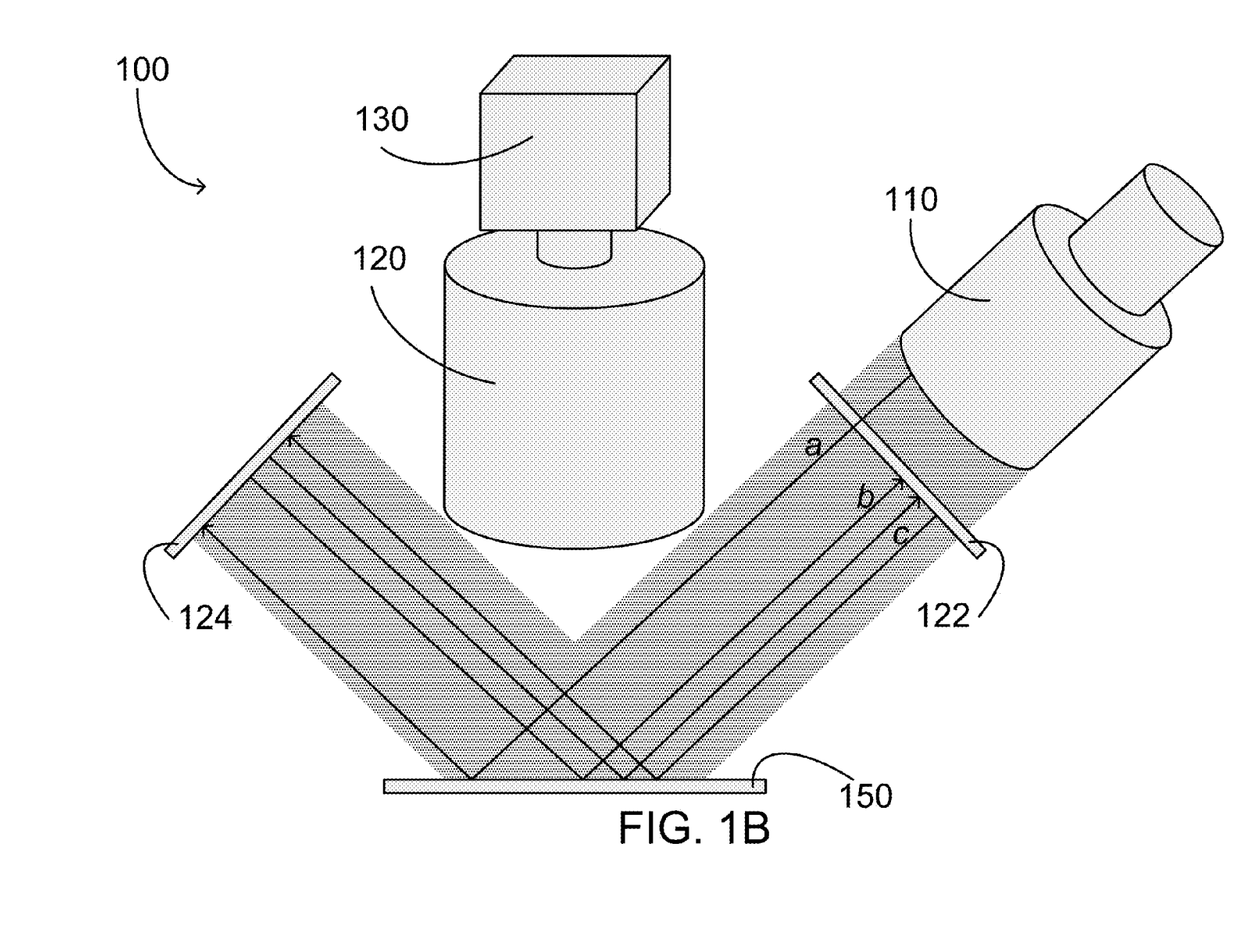
FIG. 1B provides a schematic illustrating detection of surface features of articles in accordance with an embodiment.

FIG. 1B provides a schematic for detecting and/or mapping surface features of articles with a focus on components for increasing photon flux at various surfaces (e.g., surface of article 150, photon detector array 130, etc.), illustrating an apparatus 100 comprising a photon emitter 110, an optical setup comprising optical components 120, 122, and 124, and a photon detector array 130. FIG. 1B further provides rays a, b, and c, illustrating, for example, increasing photon flux at a surface of an article 150. While not shown, the apparatus further comprises a computer or equivalent device 140, and a surface features map 160 of the surface of the article 150 in accordance FIG. 1A. The articles and apparatuses of the invention, as well as methods of the invention, are not limited to the embodiments in FIG. 1B, as additional embodiments of the invention may be realized by the features described in more detail herein.

Figure 1C:
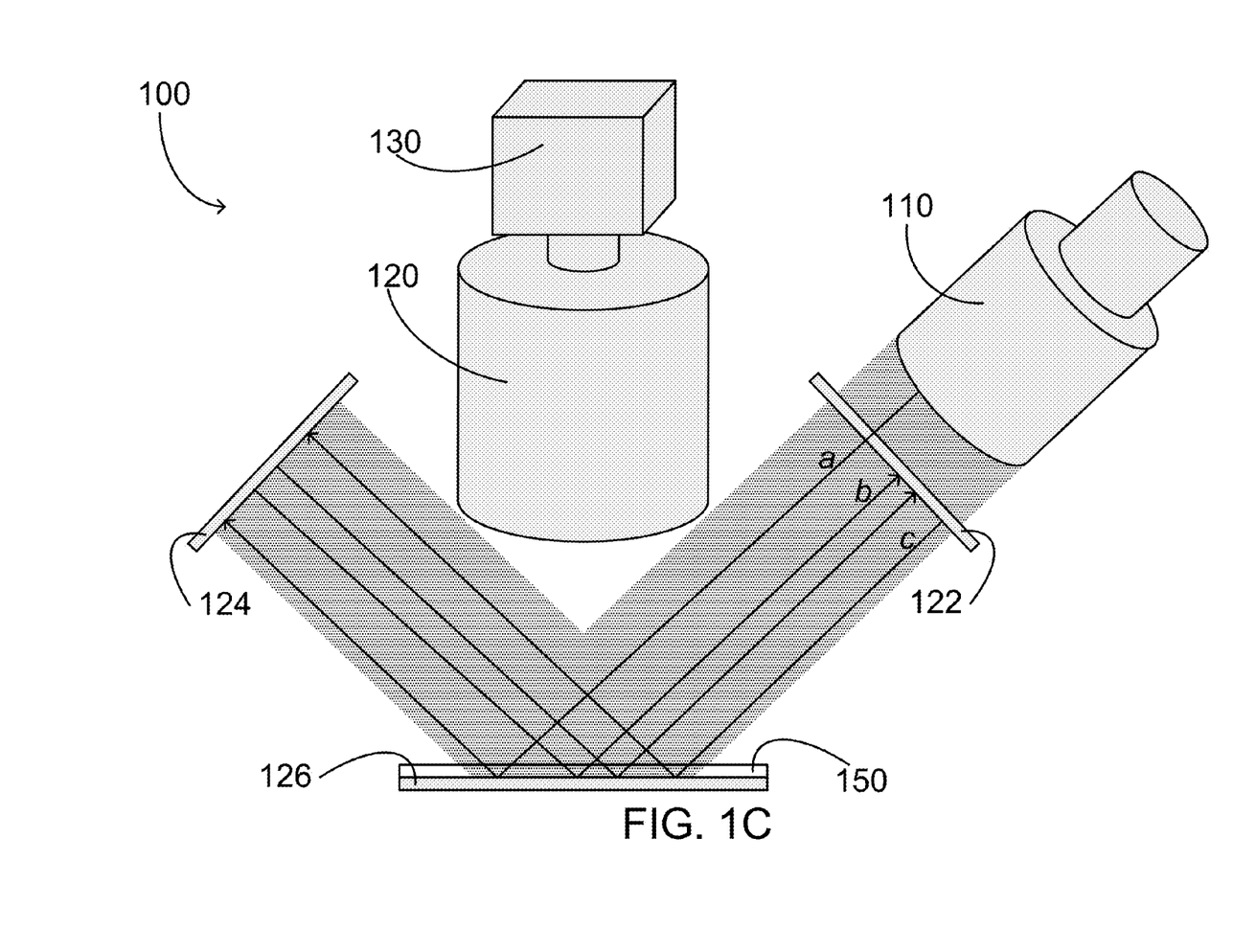
FIG. 1C provides a schematic illustrating detection of surface features of articles in accordance with an embodiment.

FIG. 1C provides a schematic for detecting and/or mapping surface features of articles with a focus on components for increasing photon flux at various surfaces (e.g., surface of article 150, photon detector array 130, etc.), illustrating an apparatus 100 comprising a photon emitter 110, an optical setup comprising optical components 120, 122, 124, and 126, and a photon detector array 130. FIG. 1C further provides rays a, b, and c, illustrating, for example, increasing photon flux at a surface of an article 150, which article 150 may be transparent. While not shown, the apparatus further comprises a computer or equivalent device 140 and a surface features map 160 of the surface of the article 150 in accordance FIG. 1A. The articles and apparatuses of the invention, as well as methods of the invention, are not limited to the embodiments in FIG. 1C, as additional embodiments of the invention may be realized by the features described in more detail herein.

An apparatus may comprise a single photon emitter (e.g., see photon emitter 110 of FIGS. 1A-1C) or a plurality of photon emitters. In some embodiments, for example, the apparatus may comprise at least 1, 2, 3, 4, 5, 6, 7, 8, 9, or 10 photon emitter(s). In some embodiments, for example, the apparatus may comprise no more than 10, 9, 8, 7, 6, 5, 4, 3, 2, or 1 photon emitter(s). Combinations of the foregoing may also be used to describe the number of photon emitters of the apparatus. In some embodiments, for example, the apparatus may comprise at least 2 photon emitters and no more than 10 photon emitters (e.g., between 2 and 10 photon emitters), such as at least 2 photon emitters and no more than 6 photon emitters (e.g., between 2 and 6 photon emitters), including at least 2 photon emitters and no more than 4 photon emitters (e.g., between 2 and 4 photon emitters). A single photon emitter may be used to emit photons onto a surface of an article, such as the entire surface of the article or some predetermined portion of the surface of the article (e.g., for gradational rotation of the article for piecewise inspection, if desired); each photon emitter of a plurality of photon emitters may be used to emit photons onto the surface of the article, such as the entire surface of the article or some predetermined portion of the surface of the article, at different times and/or at the same time in any collection of photon emitters. Further with respect to the plurality of photon emitters, each photon emitter of a plurality of photon emitters may be the same or different, or some combination thereof (e.g., at least 2 of the same photon emitter, with the remainder of photon emitters being different; at least 4 of the same photon emitter, with the remainder of photon emitters being different; etc.). In some embodiments, for example, the apparatus may comprise at least two different photon emitters, wherein the two different photon emitters are each separately configured to emit photons onto a surface of an article, such as the entire surface of the article or some predetermined portion of the surface of the article.

Whether the apparatus comprises a single photon emitter or a plurality of photon emitters, each photon emitter may emit photons onto a surface of an article at a distance and/or an angle optimized for one or more types of features, which types of features are described in more detail herein. The angle may be equal to the glancing angle, which glancing angle is the complement of the angle of incidence, and which angle of incidence is the angle between a ray comprising the emitted photons incident on the surface of the article and the normal (i.e., a line perpendicular to the surface of the article) at the point at which the ray is incident. The glancing angle may also be described as the smallest angle between a ray comprising the emitted photons incident on the surface of the article and the surface at the point at which the ray is incident.

Figure 2:
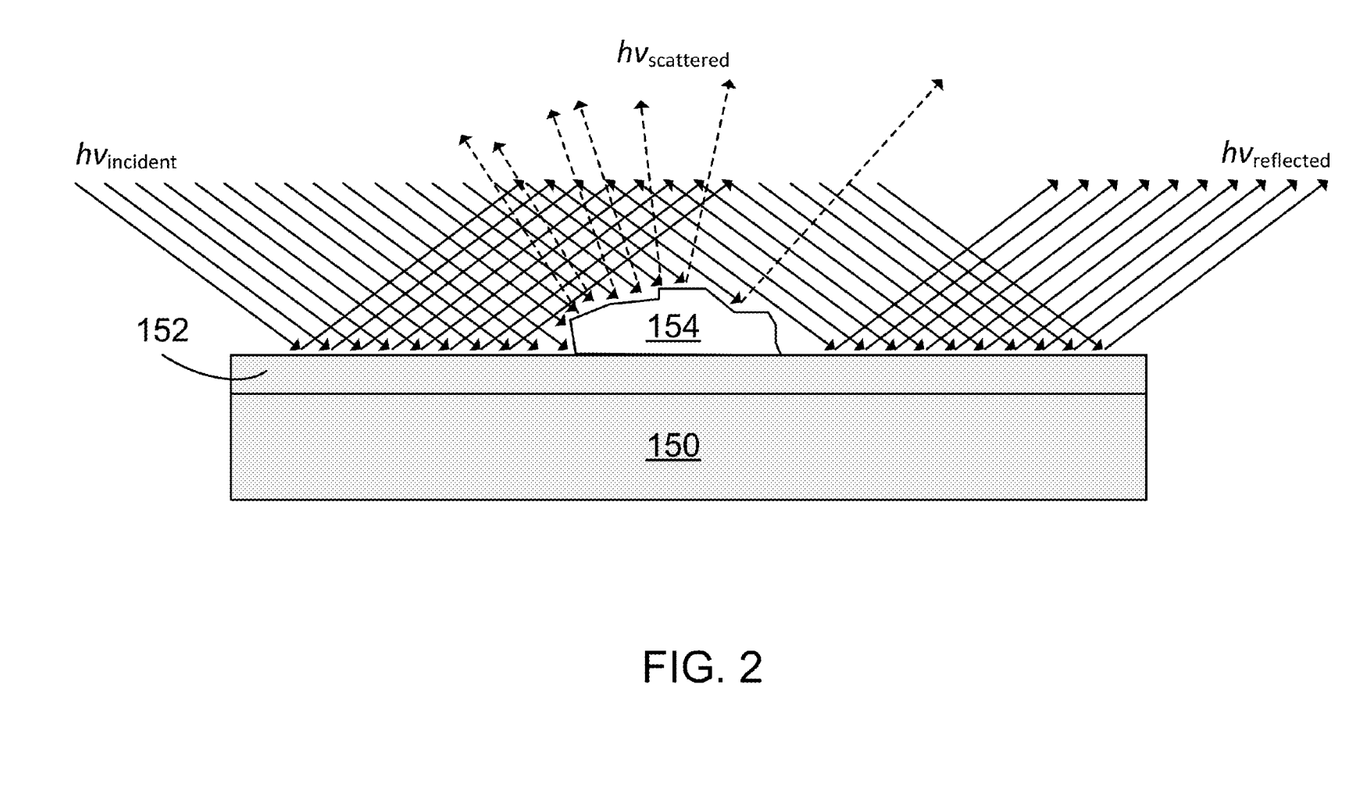
FIG. 2 provides a schematic illustrating photon scattering from a surface feature of an article in accordance with an embodiment.

FIG. 2 provides a number of rays comprising emitted photons incident on a surface 152 of an article 150 that form a glancing angle with the surface 152. FIG. 2 further provides a number of rays comprising reflected photons that form an angle of reflection with the normal to the surface, which angle of reflection is equal to the angle of incidence. FIG. 2 even further provides a number of rays comprising scattered photons from a feature 154 on the surface 152 of the article 150, which rays comprising scattered photons form various scatter angles. A photon emitter may emit photons at a glancing angle ranging from 0° to 90°, wherein a glancing angle of 0° represents the photon emitter emitting photons onto the surface of the article from a side of the article, and wherein a glancing angle of 90° represents the photon emitter emitting photons onto the surface of the article from directly above the article. In some embodiments, for example, a photon emitter may emit photons onto a surface of an article such that the glancing angle is at least 0°, 5°, 10°, 15°, 20°, 25°, 30°, 35°, 40°, 45°, 50°, 55°, 60°, 65°, 70°, 75°, 80°, 85°, or 90°. In some embodiments, for example, a photon emitter may emit photons onto a surface of an article such that the glancing angle is no more than 90°, 85°, 80°, 75°, 70°, 65°, 60°, 55°, 50°, 45°, 40°, 35°, 30°, 25°, 20°, 15°, 10°, 5°, or 0°. Combinations of the foregoing may also be used to describe the glancing angle at which a photon emitter may emit photons onto a surface of an article. In some embodiments, for example, a photon emitter may emit photons onto a surface of an article such that the glancing angle is at least a 0° and no more than 90° (i.e., between 0° and 90°), such as at least 0° and no more than 45° (i.e., between 0° and 45°), including at least 45° and no more than 90° (i.e., between 45° and 90°).

A photon emitter may emit photons onto a surface of an article, such as the entire surface or some predetermined portion of the surface (e.g., for gradational rotation of the article for piecewise inspection, if desired). The photon emitter may further emit photons onto the entire surface of the article or some predetermined portion of the surface such that the entire surface or the predetermined portion of the surface is uniformly or homogenously illuminated. Uniformly illuminating the entire surface of the article or some predetermined portion of the surface includes, but is not limited to, subjecting the entire surface of the article or some predetermined portion of the surface of the article to the same or about the same quantity of photons (e.g., photon flux) per unit time, the same or about the same photon energy per unit time (e.g., photon power), and/or the same or about the same photon power per unit area (e.g., photon flux density). In radiometric terms, uniformly illuminating includes, but is not limited to, subjecting the entire surface of the article or some predetermined portion of the surface of the article to the same or about the same quantity of light per unit time, the same or about the same radiant energy per unit time (e.g., radiant power or radiant flux), and/or the same or about the same radiant power per unit area (e.g., irradiance or radiant flux density).

With the appreciation that photons are the elementary particles of electromagnetic radiation or light, a photon emitter or light source may provide light comprising a relatively wide range of wavelengths (e.g., whole spectrum, broad spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); light comprising a relatively wide range of frequencies (e.g., whole spectrum, broad spectrum, ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic); polarized (e.g., linear polarization, circular polarization, etc.) light, partially polarized light, or nonpolarized light; and/or light with different degrees of temporal and/or spatial coherence ranging from coherent light (e.g., laser) to noncoherent light. A photon emitter or light source may be used in conjunction with one or more optical components of an optical setup to provide light having any of the foregoing qualities. Wavelength filters, for example, may be used in conjunction with a photon emitter or light source to provide light comprising a relatively wide range of wavelengths or frequencies, a relatively narrow range of wavelengths or frequencies, or a particular wavelength or frequency. Polarization filters, for example, may also be used in conjunction with a photon emitter or light source to provide light of a desired polarization including polarized light, partially polarized light, or nonpolarized light.

In view of the foregoing, a photon emitter or light source may comprise a lamp such as a flash lamp, including a high-speed flash lamp, configured to minimize vibration while detecting photons scattered from surface features of an article with a photon detector array. In some embodiments, for example, a photon emitter or light source may comprise a high-speed Xe flash lamp such as a 500 W Xe flash lamp to minimize vibration while detecting photons scattered from surface features of an article with a photon detector array.

Also in view of the foregoing, a photon emitter or light source may comprise a collimated light source such as a laser, including a combination of lasers, configured to emit photons onto a surface of an article at one or more angles. In some embodiments, for example, a combination of lasers may be provided to a laser beam shaper such that the combination of lasers emits photons onto a surface of an article at one angle. In some embodiments, for example, a combination of lasers may be provided to a laser beam shaper such that the combination of lasers emits photons onto a surface of an article at multiple angles. In some embodiments, for example, at least 2, 4, 6, 8, 10, 12, 14, 16, 18, 20, 22, 24, 26, 28, or 30 lasers, or even more than 30 lasers, may be provided to a laser beam shaper such that the combination of lasers emits photons onto a surface of an article at one or more angles. In some embodiments, for example, no more than 30, 28, 26, 24, 22, 20, 18, 16, 14, 12, 10, 8, 6, 4, or 2 lasers may be provided to a laser beam shaper such that the combination of lasers emits photons onto a surface of an article at one or more angles. Combinations of the foregoing may also be used to describe combinations of lasers provided to a laser beam shaper. In some embodiments, for example, at least 2 lasers and no more than 30 lasers (e.g., between 2 and 30 lasers), such as at least 10 lasers and no more than 30 lasers (e.g., between 10 and 30 lasers), including at least 20 lasers and no more than 30 lasers (e.g., between 20 and 30 lasers), and further including at least 24 lasers and no more than 28 lasers (e.g., between 24 and 28 lasers) may be provided to a laser beam shaper such that the combination of lasers emits photons onto a surface of an article of an article at one or more angles.

Further in view of the foregoing, a photon emitter or light source may comprise a two-dimensional light source such as a combination of point light sources, including a linear combination or array, an arcuate combination or array, etc. of point light sources configured to emit photons onto a surface of an article. In some embodiments, for example, a two-dimensional light source may comprise a combination of at least 10, 20, 40, 60, 80, 100, 110, 120, 140, 160, 180, or 200 point light sources, or even more than 200 point sources. In some embodiments, for example, a two-dimensional light source may comprise a combination of no more than 200, 180, 160, 140, 120, 100, 80, 60, 40, 20, or 10 point light sources. Combinations of the foregoing may also be used to describe two-dimensional light sources comprising combinations of point light sources. In some embodiments, for example, a two-dimensional light source may comprise a combination of at least 10 and no more than 200 (e.g., between 10 and 200) point light sources, such as at least 40 and no more than 160 (e.g., between 40 and 160) point light sources, including at least 60 and no more than 140 (e.g., between 60 and 140) point light sources, and further including at least 80 and no more than 120 (e.g., between 80 and 120) point light sources. Such point light sources may be combined in rows and columns of a two-dimensional array, including linearly combined to form a two-dimensional light source such as a strip light. Such point light sources may be arcuately combined to form a two-dimensional light source such as a ring light. In some embodiments, for example, a photon emitter or light source may comprise a two-dimensional light source comprising at least 60 point light sources, such as a ring light comprising at least 60 point light sources, including a ring light comprising at least 60 light-emitting diodes ("LEDs"), and further including a ring light comprising at least 100 LEDs. A two-dimensional light source comprising LEDs may comprise white LEDs, wherein each LED has a power of at least 10 mW. An LED-based ring light may enhance features such as scratches (e.g., circumferential scratches) and/or voids in surfaces of articles, especially when the LED-based ring light is configured to emit photons onto the surfaces of the articles with lower angles (e.g., glancing angle equal to or less than 45°).

The apparatus may further comprise an optical setup (e.g., optical setup comprising one or more of optical components 120, 122, 124, and 126 of FIGS. 1A-1C), which optical setup may manipulate photons emitted from one or more photon emitters, photons reflected from a surface of an article, and/or photons scattered from surface features of an article. With the appreciation that photons are the elementary particles of electromagnetic radiation or light, the optical setup may manipulate light emitted from one or more photon emitters, light reflected from a surface of an article, and/or light scattered from surface features of an article. The optical setup up may comprise any of a number of optical components positioned before the article such that the optical components may be used to manipulate photons emitted from one or more photon emitters before uniformly or homogenously illuminating the entire surface or the predetermined portion of the surface of the article. Alternatively, or in addition, the optical setup up may comprise any of a number of optical components positioned after the article such that the optical components may be used to manipulate photons reflected from the surface of the article or scattered from surface features of the article. Alternatively, or in addition, an optical component comprising the article (e.g., article 150 of FIG. 1B) may be used to manipulate (e.g., reflect) photons. The forgoing optical components may include, but are not limited to, optical components such as lenses, filters, gratings, and mirrors, which mirrors include articles comprising optically smooth surfaces.

With respect to optical components such as lenses, the optical setup may comprise a single lens or a plurality of lenses, including, but not limited to, a combination of a lens coupled to a photon detector array (e.g., a lens-and-photon-detector-array combination comprising lens 120 and photon detector array 130 of FIGS. 1A-1C) configured for collecting and detecting photons scattered from surface features of articles. The lens coupled to the photon detector array may have an entrance pupil and an exit pupil, and additional optical components such as lenses (e.g., lenses in addition to the lens coupled to the photon detector array), filters, gratings, and mirrors, may be positioned in any combination of one or more optical components at or near the entrance pupil of the lens coupled to the photon detector array, at or near the exit pupil of the lens coupled to the photon detector array (i.e., in-between the exit pupil of the lens and the photon detector array), or some combination thereof to manipulate photons scattered from surface features of articles. The lens coupled to the photon detector array may be an objective lens, such as a telecentric lens, including an object-space telecentric lens (i.e., entrance pupil at infinity), an image-space telecentric lens (i.e., exit pupil at infinity), or a double telecentric lens (i.e., both pupils at infinity). Coupling a telecentric lens to a photon detector array reduces errors with respect to the position of surface features of articles, reduces distortion of surface features of articles, enables quantitative analysis of photons scattered from surface features of articles, which quantitative analysis includes integration of photon scattering intensity distribution for size determination of surface features of articles.

With respect to optical components such as filters, the optical setup may comprise a filter or a plurality of filters including, but not limited to, one or more wavelength filters, band-pass filters, polarization filters, coherence filters, periodic array-tuned filters, and phase filters. As described herein, when one or more of such filters is positioned before an article to manipulate photons emitted from a photon emitter, photons/light having any of a number of different qualities may be provided to a surface of the article. When one or more of such filters is positioned after an article to manipulate photons scattered from surface features of the article, the one or more filters may be used for distinguishing between surface features of the article. For example, a wavelength filter may be used to distinguish between surface features known to differentially scatter photons with respect to wavelength; a polarization filter may be used to distinguish between surface features known to differentially scatter photons with respect to polarization; a coherence filter may be used to distinguish between surface features known to differentially scatter photons with respect to coherence; and a phase filter or waveplate may be used to distinguish between surface features known to differentially scatter photons with respect to phase. In some embodiments, for example, an optical component such as a filter may be positioned at or near the entrance pupil of a lens (e.g., telecentric lens) coupled to a photon detector array. In some embodiments, for example, an optical component such as a filter may be positioned at or near the exit pupil of a lens (e.g., telecentric lens) coupled to a photon detector array.

Without being bound by theory, an article such as a magnetic recording medium (e.g., hard disk for a hard disk drive) comprises a perfectly flat surface with zero geometric aberrations. A fraction of the surface of the article (e.g., surface features of the article) will scatter photons incident on the surface of the article to the order of 1 part in $10^{14}$. As such, most of the photons incident on the surface of the article are not used. Scattering intensity $I_{scatter}$ of photons scattered from surface features of articles is nearly described by the following equation:

$$I_{scatter} \approx I_{incident} \frac{k\pi^4 \phi^6 f(n)}{\lambda_{incident}^4 d^2},$$

wherein is the characteristic diameter of a surface feature, and wherein $\lambda_{incident}$ and $I_{incident}$ are respectively the wavelength and intensity of the incident photon flux. In view of the foregoing equation, while holding the remaining constants, coefficients, and/or parameters constant, an increase in $I_{incident}$ leads to an increase in $I_{scatter}$ of photons, which increase in $I_{incident}$ may be effected by recycling photons incident on the surface of the article using optical components such as optical components 122, 124, and/or 124 of FIGS. 1B and 1C, which optical components may include reflective surfaces such as mirrors.

With respect to optical components comprising reflective surfaces such as mirrors, the optical setup may comprise one or more mirrors of any curvature including, but not limited to, one or more optical-grade mirrors and one-way mirrors, including articles comprising optically smooth surfaces. As illustrated in FIGS. 1B and 1C, one or more mirrors may be positioned about an apparatus, such as in a light path before an article (i.e., between a photon emitter and the article) (e.g., one-way mirror 122 of FIGS. 1B and 1C); in the light path after an article (e.g., mirror 124 of FIGS. 1B and 1C); in the light path under the article, for example, parallelly proximate to a transparent article (e.g., mirror 126 in FIG. 1C); and in combinations thereof. In some embodiments, for example, the apparatus may be configured as illustrated in FIG. 1B, FIG. 1C, or as in FIG. 1B or FIG. 1C but without the one-way mirror between the photon emitter and the article. In view of FIGS. 1B and 1C, and without being bound by theory, the increase in $I_{incident}$ for a perfectly parallel beam of photons follows a geometric series with a convergence consistent with the reflection coefficient of a one-way mirror (e.g., one-way mirror 122 of FIGS. 1B and 1C). In practice, some divergence is expected, such that the increase in $I_{incident}$ follows a geometric series with a more rapid convergence consistent with the one-way mirror and the divergence angle of the beam of photons. As such, in some embodiments, the one or more reflective surfaces (e.g., mirrors) are operable to increase the photon flux and/or $I_{incident}$ at a surface of an article by at least a factor of 2, 3, 4, 5, 6, 7, 8, 9, or 10 over the photon flux and/or $I_{incident}$ at the surface of the article provided by the photon emitter in the absence of the one or more reflective surfaces. In some embodiments, the one or more reflective surfaces (e.g., mirrors) are operable to increase the photon flux and/or $I_{scatter}$ at a photon detector array by at least a factor of 2, 3, 4, 5, 6, 7, 8, 9, or 10 over the photon flux and/or $I_{scatter}$ at the photon detector array in the absence of the one or more reflective surfaces. Such an increase in photon flux, $I_{incident}$, and/or $I_{scatter}$ optionally allows for use of lower-power photon emitters, which may translate into higher reliability, lower operating temperatures, and lower cost than higher-power photon emitters.

Turning back to FIG. 1B, which provides a schematic for detecting and/or mapping surface features of articles with a focus on components for increasing photon flux at various surfaces (e.g., a surface of article 150, a photon detector array 130, etc.), the apparatus 100 may comprise a photon emitter 110, an optical setup comprising optical components 120, 122, and 124, and a photon detector array 130, wherein the optical component 120 comprises a lens (e.g., telecentric lens), the optical component 122 comprises a reflective surface such as a one-way mirror, and the optical component 124 comprises a reflective surface such as a mirror. In some embodiments, the transmittable side of the one-way mirror transmits at least 50%, 60%, 70%, 75%, 80%, 85%, 90%, or 95% of incident photons. FIG. 1B further provides rays a, b, and c, each of which rays represents a beam of photons. Ray a illustrates, for example, photons may be emitted from the photon emitter 110, pass through the transmittable side of the one-way mirror 122, strike the surface of the article 150, and reflect off the surface of the article 150 toward the mirror 124. Ray b illustrates, for example, photons may reflect off the mirror 124, strike the surface of the article 150, and reflect off the surface of the article 150 toward the half-mirror 122. Ray c illustrates, for example, photons may reflect off the reflective side of the half-mirror 122, strike the surface of the article 150, and reflect off the surface of the article 150 toward the mirror 124. In this way, photons may be emitted from the photon emitter 110 and reflected among various reflective surfaces (e.g., the half-mirror 122, the mirror 124, and the surface of the article 150) to recycle the photons and increase the photon flux at the surface of the article 150 and, in conjunction, at the photon detector array 130.

Turning back to FIG. 1C, which provides a schematic for detecting and/or mapping surface features of articles with a focus on components for increasing photon flux at various surfaces (e.g., a surface of transparent article 150, a photon detector array 130, etc.), the apparatus 100 may comprise a photon emitter 110, an optical setup comprising optical components 120, 122, 124, and 126, and a photon detector array 130, wherein the optical component 120 comprises a lens (e.g., telecentric lens), the optical component 122 comprises a reflective surface such as a one-way mirror, the optical component 124 comprises a reflective surface such as a mirror, and the optical component 126 comprises a reflective surface such as a mirror. In some embodiments, the transmittable side of the one-way mirror transmits at least 50%, 60%, 70%, 75%, 80%, 85%, 90%, or 95% of incident photons. FIG. 1C further provides rays a, b, and c, each of which rays represents a beam of photons. Ray a illustrates, for example, photons may be emitted from the photon emitter 110, pass through the transmittable side of the one-way mirror 122, pass through the transparent article 150, and reflect off the surface of the mirror 126 toward the mirror 124. Ray b illustrates, for example, photons may reflect off the mirror 124, pass through the transparent article 150, and reflect off the surface of the mirror 126 toward the half-mirror 122. Ray c illustrates, for example, photons may reflect off the reflective side of the half-mirror 122, pass through the transparent article 150, and reflect off the surface of the mirror 126 toward the mirror 124. In this way, photons may be emitted from the photon emitter 110 and reflected among various reflective surfaces (e.g., the half-mirror 122, the mirror 124, and the surface of the article 150) to recycle the photons and increase the photon flux at the surface of the article 150 and, in conjunction, at the photon detector array 130.

To detect photons scattered from surface features of articles, an apparatus may further comprise a single photon detector array (e.g., see photon detector array 130 of FIG. 1A) comprising a plurality of photon detectors or a plurality of photon detector arrays, each comprising a plurality of photon detectors. In some embodiments, for example, the plurality of photon detector arrays may comprise at least 2, 3, 4, 5, 6, 7, 8, 9, or 10 photon detector arrays. In some embodiments, for example, the plurality of photon detector arrays may comprise no more than 10, 9, 8, 7, 6, 5, 4, 3, or 2 photon detector arrays. Combinations of the foregoing may also be used to describe the plurality of photon detector arrays. In some embodiments, for example, the plurality of photon detector arrays may comprise at least 2 photon detector arrays and no more than 10 photon detector arrays (e.g., between 2 and 10 photon detector arrays), such as at least 2 photon detector arrays and no more than 5 photon detector arrays (e.g., between 2 and 5 photon detector arrays). Further with respect to the plurality of photon detector arrays, each photon detector array of the plurality of photon detector arrays may be the same or different, or some combination thereof (e.g., at least 2 of the same photon detector array, with the remainder of photon detector arrays being different; at least 3 of the same photon detector array, with the remainder of photon detector arrays being different; etc.).

Whether the apparatus comprises a single photon detector array or a plurality of photon detector arrays, each photon detector array may be oriented to detect photons scattered from surface features of an article at a distance and/or an angle for an optimum acceptance of photons (e.g., maximum acceptance of photons with minimum background noise) scattered from one or more types of features, which types of features are described in more detail herein. Likewise, a lens-and-photon-detector-array combination may be oriented to collect and detect photons scattered from surface features of an article at a distance and/or an angle for an optimum acceptance of photons scattered from one or more types of features. Such an angle may be the angle between a ray comprising the center line axis of the lens and/or the photon detector array the extended to the surface of the article and the normal (i.e., a line perpendicular to the surface of the article) at the point at which the ray is extended. The angle, optionally in combination with an aperture that may be variably sized to accept a larger or smaller angle of scattered photons, or optionally in combination with an aperture that may be optimally sized for maximum acceptance of scattered photons with minimum background noise, may allow for acceptance of scattered photons respectively having a plurality of scatter angles, which scattered photons may respectively be scattered from one or more types of features. A scatter angle may be different than the angle of reflection, which angle of reflection is equal to the angle of incidence as described herein. FIG. 2 provides a number of rays comprising photons scattered from a feature 154 on a surface 152 of an article 150, which rays represent various scatter angles.

In view of the foregoing, a photon detector array or lens-and-photon-detector-array combination may be oriented at an angle ranging from 0° to 90°, inclusive, wherein an angle of 0° represents orientation of the photon detector array or the lens-and-photon-detector-array combination at a side of an article, and wherein an angle of 90° represents orientation of the photon detector array or lens-and-photon-detector-array combination directly above the article. In some embodiments, for example, a photon detector array or lens-and-photon-detector-array combination may be oriented at an angle of at least 0°, 5°, 10°, 15°, 20°, 25°, 30°, 35°, 40°, 45°, 50°, 55°, 60°, 65°, 70°, 75°, 80°, 85°, or 90°. In some embodiments, for example, a photon detector array or lens-and-photon-detector-array combination may be oriented at an angle of no more than 90°, 85°, 80°, 75°, 70°, 65°, 60°, 55°, 50°, 45°, 40°, 35°, 30°, 25°, 20°, 15°, 10°, or 5°, or 0°. Combinations of the foregoing may also be used to describe the angle at which the photon detector array or lens-and-photon-detector-array combination may be oriented. In some embodiments, for example, a photon detector array or lens-and-photon-detector-array combination may be oriented at an angle of at least a 0° and no more than a 90° (i.e., between 0° and 90°), such as least 0° and no more than 45° (i.e., between 0° and 45°) or at least 45° and no more than 90° (i.e., between 45° and 90°).

The photon detector array, optionally in combination with a lens (e.g., telecentric lens), may detect photons scattered from surface features of an article, such as the entire surface of the article or some predetermined portion of the surface of the article. The photon detector array, optionally in combination with a lens (e.g., telecentric lens), may detect photons scattered from surface features of an article, such as the entire surface of the article or some predetermined portion of the surface of the article, while oriented at a distance and/or an angle for an optimum acceptance of photons (e.g., maximum acceptance of photons with minimum background noise) scattered from one or more types of features. As provided herein, the angle for an optimum acceptance of photons scattered from one or more types of features may allow for acceptance of scattered photons respectively having a plurality of scatter angles, which scattered photons may respectively be scattered from one or more types of features.

With the appreciation that photons are the elementary particles of electromagnetic radiation or light, a photon detector array or light detector array may detect light comprising a relatively wide range of wavelengths (e.g., whole spectrum, broad spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); light comprising a relatively wide range of frequencies (e.g., whole spectrum, broad spectrum, ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic); polarized (e.g., linear polarization, circular polarization, etc.) light, partially polarized light, or nonpolarized light; and/or light with different degrees of temporal and/or spatial coherence ranging from coherent light (e.g., laser) to noncoherent light. As discussed herein, a photon detector array or light detector array may be used in conjunction with one or more optical components of an optical setup to detect light having any of the foregoing qualities.

The photon detector array may comprise a plurality of pixel sensors, which pixel sensors, in turn, may each comprise a photon detector (e.g., a photodiode) coupled to a circuit comprising a transistor configured for amplification. Features of a photon detector array comprising such pixel sensors include, but are not limited to, low temperature operation (e.g., down to −40° C.), low electron noise (e.g., 2-10 $e^-$ RMS; 1 $e^-$ RMS; <1 $e^-$ RMS; etc.), wide dynamic range (e.g., 30,000:1, 8,500:1; 3,000:1; etc.), and/or decreased photon/light collection time. A photon detector array may comprise a large number of pixel sensors (e.g., ≥1,000,000 or ≥1M pixel sensors) arranged in rows and columns of a two-dimensional array, wherein each pixel sensor comprises a photon detector coupled to an amplifier. In some embodiments, for example, a photon detector array may comprise at least 1M, 2M, 3M, 4M, 5M, 6M, 7M, 8M, 9M, 10M, or more, pixel sensors arranged in rows and columns of a two-dimensional array. In some embodiments, for example, a photon detector array may comprise no more than 10M, 9M, 8M, 7M, 6M, 5M, 4M, 3M, 2M, or 1M, pixel sensors arranged in rows and columns of a two-dimensional array. Combinations of the foregoing may also be used to describe the number of pixel sensors in a photon detector array. In some embodiments, for example, a photon detector array may comprise at least 1M and no more than 10M (e.g., between 1M and 10M) pixel sensors arranged in rows and columns of a two-dimensional array, such as at least 1M and no more than 8M (e.g., between 1M and 8M) pixel sensors, including at least 1M and no more than 6M (e.g., between 1M and 8M) pixel sensors, further including at least 2M and no more than 6M (e.g., between 1M and 8M) pixel sensors, and even further including at least 2M and no more than 5M (e.g., between 2M and 5M) pixel sensors.

Due to surface reflections of surface features of articles and/or small angle scattering (e.g., 4π scattering), surface features may appear much larger in size enabling pixel sensors larger the than surface features to be used. In some embodiments, for example, a photon detector array may comprise micrometer-sized (i.e., admits of µm units as measured) pixel sensors at least 1 µm, 2 µm, 3 µm, 4 µm, 5 µm, 6 µm, 7 µm, 8 µm, 9 µm, or 10 µm in their smallest dimension. In some embodiments, for example, a photon detector array may comprise micrometer-sized pixel sensors no more than 10 µm, 9 µm, 8 µm, 7 µm, 6 µm, 5 µm, 4 µm, 3 µm, 2 µm, or 1 µm in their smallest dimension. Combinations of the foregoing may also be used to describe dimensions of micrometer-sized pixel sensors in photon detector arrays. In some embodiments, for example, a photon detector array may comprise micrometer-sized pixel sensors at least 1 µm and no more than 10 µm (e.g., between 1 µm and 10 µm) in their smallest dimension, such as at least 1 µm and no more than 7 µm (e.g., between 1 µm and 7 µm), including at least 4 µm and no more than 10 µm (e.g., between 4 µm and 10 µm), and further including at least 4 µm and no more than 7 µm (e.g., between 4 µm and 7 µm). Such micrometer-sized pixel sensors may be used in the apparatus for detecting and/or mapping surface features of articles, wherein the surface features are more than 100 times smaller than the micrometer-sized pixel sensors.

In view of the foregoing, the single photon detector array or the plurality of photon detector arrays may each comprise a complementary metal-oxide semiconductor ("CMOS") or a scientific complementary metal-oxide semiconductor ("sCMOS"), each of which may optionally be part of CMOS camera or a sCMOS camera, respectively. Alternatively, the single photon detector array or the plurality of photon detector arrays may each comprise a charge-coupled device ("CCD"), which may optionally be part of CCD camera. While a CCD-based photon detector array might have a slower recording speed than a CMOS-based or sCMOS-based photon detector array, a CCD-based photon detector array may be desirable in applications requiring less electronic and/or image noise. A CCD-based photon detector array, including an electron-multiplying CCD ("EMCCD"), may also be desirable in certain applications having low-light conditions. Furthermore, a plurality of photon detector arrays is not limited to combinations of either CMOS/sCMOS-based photon detector arrays or CCD-based photon-detector arrays, as a plurality of photon detector arrays may comprise a combination of any of a number of CMOS/sCMOS-based photon detector arrays and CCD-based photon-detector arrays in applications that benefit from employing each type of technology. In some embodiments, for example, a CMOS/sCMOS-based photon detector array may be used to detect photons scattered from surface features of articles in certain applications having sufficient light for the CMOS/sCMOS-based photon detector array, while a CCD/EMCCD-based photon detector array may be used to detect photons scattered from surface features of articles in certain applications having too little light for the CMOS/sCMOS-based photon detector array.

Figure 3:
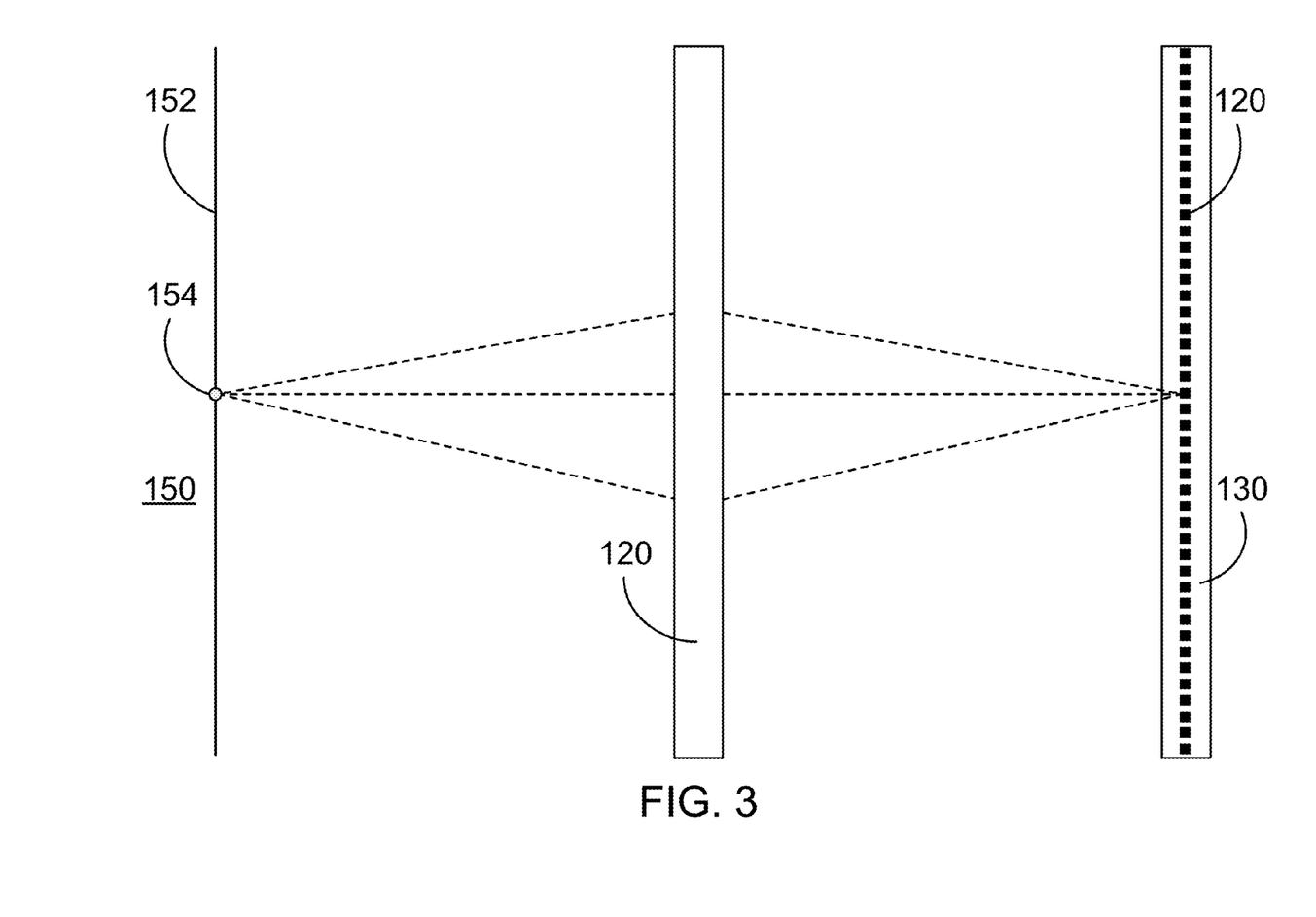
FIG. 3 provides a schematic illustrating photons scattering from a surface feature of an article, through an optical component, and onto a photon detector array in accordance with an embodiment.
Figure 4:
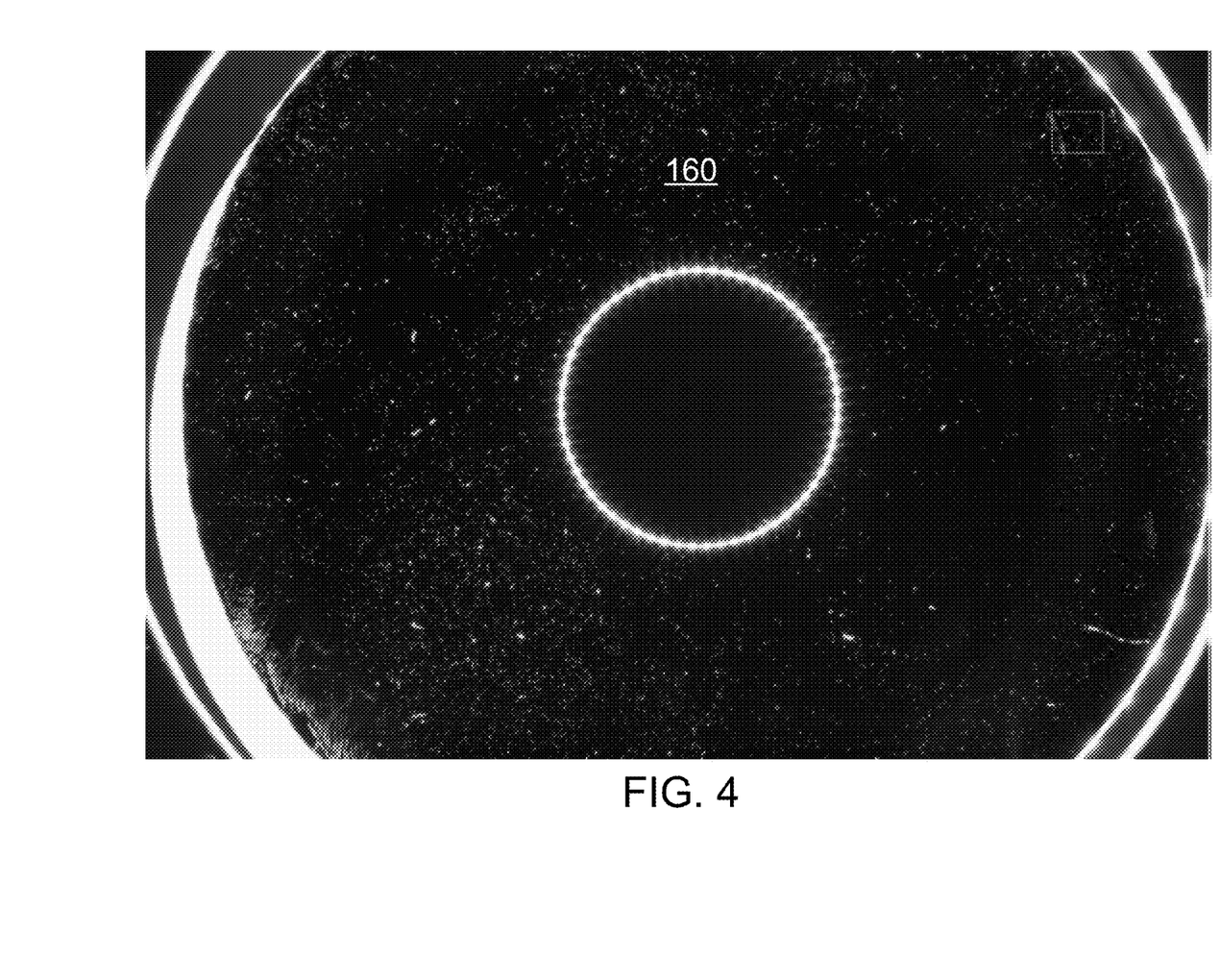
FIG. 4 provides an image of a surface features map of an article in accordance with an embodiment.

FIG. 3 provides a schematic for detection of surface features of an article, illustrating a close-up, cross-sectional view of an apparatus comprising an optical setup and a photon detector array. As shown, article 150 comprises a surface 152 and at least surface feature 154. Photons may be scattered by the surface feature 154 and collected and detected by a combination comprising a lens 120 coupled to a photon detector array 130, which combination may be positioned at a distance and/or an angle for a an optimum acceptance of photons (e.g., maximum acceptance of photons with minimum background noise) scattered from one or more types of features. The optical setup, which may comprise a telecentric lens (e.g., lens 120 of FIGS. 1A-1C), may collect and focus the photons scattered from the surface feature 154 onto one or more pixel sensors 132 of photon detector array 130, which one or more pixel sensors may each comprise a photon detector coupled to an amplifier (e.g., CMOS/sCMOS-based photon detector array; EMCCD-based photon detector array; etc.). The one or more pixel sensors 132, each of which corresponds to a particular, fixed area of an article's surface and a pixel in a map of the article's surface features, may provide one or more signals to a computer or equivalent device for mapping or otherwise determining the position of the surface feature 154. The computer or equivalent device may subsequently use pixel interpolation for further mapping the surface feature 154.

Depending upon factors that may include the type of article, the type of surface features (e.g., particle, stain, scratch, void, etc.), and the like, it may be desirable at times to increase detection time of a single photon detector array or a plurality of photon detector arrays to detect more photons for detecting and/or mapping surface features of articles. In some embodiments, for example, detection time of a single photon detector array or a plurality of photon detector arrays may be increased to detect more photons. In such embodiments, a CCD-based photon detector array, including an electron-multiplying EMCCD may be used to further detect more photons. Alternately, or in addition, it may be desirable to increase the number of photons (e.g., photon energy) emitted from a single photon emitter or a plurality of photon emitters to provide an increase in photons scattered for detecting and/or mapping surface features of articles. Such an increase in photon energy may be with respect to unit time for increased photon power, or with respect to unit area for increased photon flux density. Alternately to one or both of increasing the photon energy or detection time, or in addition to increasing the photon energy and detection time, it may be desirable at times to minimize background noise including stray light from one or more photon emitters, background light, and/or background fluorescent radiation.

The apparatus may further comprise one or more computers or equivalent devices (e.g., devices that include primary and/or secondary memory and one or more processing elements operable to carry out arithmetic and logical operations), including, but not limited to, servers, workstations, desktop computers, nettops, laptops, netbooks, and mobile devices such as tablets and smartphones, which computers or equivalent devices may contain application-specific integrated circuits ("ASIC"s), field-programmable gate arrays ("FPGA"s), etc. The computers or equivalent devices may include a computer-readable storage medium for instructions making the apparatus operable to, but not limited to, but not limited to, convey each article to the apparatus for inspection; position each article for inspection, optionally including gradational rotation of the article for piecewise inspection; hold or otherwise maintain the position of each article for inspection; insert optical components into the optical setup, for example, using a mechanical actuator; position optical components for inspection; adjust optical components (e.g., focus lenses) and/or tune optical components (e.g., piezoelectric-based wavelength filters; piezoelectric-based polarization filters; etc.) for inspection; remove optical components from the optical setup; move each photon emitter into position for inspection, wherein the position for inspection may include a photon emitter-article distance and/or angle (e.g., glancing angle) optimized for one or more types of features; switch each photon emitter on and off, or otherwise between modes for emitting photons and not emitting photons; move each photon detector array into position for inspection, wherein the position for inspection may include a photon detector array-article distance and/or angle (e.g., scatter angle) optimized for one or more types of features; switch each photon detector array on and off, or otherwise between modes for detecting photons and not detecting photons; synchronize each photon emitter with each photon detector in accordance with a photon emission-photon detection scheme; process photon detector array signals from scattered photons, optionally including pixel interpolation for better accuracy (e.g., 10× better than pixel size) with respect to the position of surface features; map or otherwise determine the position of surface features of articles from photon detector array signals or processed photon detector array signals (e.g., photon scattering intensity distributions); quantitatively and/or qualitatively characterize surface features of articles; catalog surface features of articles; and determine trends with respect to surface features of articles.

The apparatus may be configured for detecting and/or mapping surface features of articles, wherein the surface features are nanometer-sized (i.e., admits of nm units as measured) or smaller in their smallest dimension (e.g., length, width, height, or depth, depending on the surface feature), which surface features may be smaller than the wavelength of photons emitted from a photon emitter of the apparatus. However, the apparatus is not limited to surface features of articles that are nanometer-sized or smaller, as the apparatus may be configured for detecting and/or mapping surface features of articles, wherein the surface features are micrometer-sized (i.e., admits of µm units as measured) or larger. In some embodiments, for example, the apparatus may be configured for detecting and/or mapping surface features of articles, wherein the surface features are smaller than 500 nm, 250 nm, 200 nm, 150 nm, 125 nm, 110 nm, 100 nm, 90 nm, 80 nm, 70 nm, 60 nm, 50 nm, 40 nm, 30 nm, 20 nm, 10 nm, or 1 nm (10 Å) in their smallest dimension, or even smaller, such as surface features of articles smaller than 9 Å, 8 Å, 7 Å, 6 Å, 5 Å, 4 Å, 3 Å, 2 Å, or 1 Å in their smallest dimension. In view of the foregoing, and in some embodiments, for example, the apparatus may be configured for detecting and/or mapping surface features of articles, wherein the surface features are between 0.1 nm and 1000 nm, such as between 0.1 nm and 500 nm, including between 0.1 nm and 250 nm, and further including between 0.1 nm and 100 nm, and even further including between 0.1 nm and 80 nm. Furthermore, the apparatus may be configured for detecting and/or mapping sub-surface features, such as subsurface defects, wherein the subsurface features have a depth more than 1 nm, 2 nm, 3 nm, 4 nm, 5 nm, 6 nm, 7 nm, 8 nm, 9 nm, or 10 nm, or deeper.

The apparatus may be configured for detecting and/or mapping surface features of articles, including surface and/or subsurface defects comprising particle contamination in which the particles are nanometer-sized (i.e., admits of nm units as measured) or smaller in their smallest dimension (e.g., length, width, or height). In some embodiments, for example, the apparatus may be configured for detecting and/or mapping surface and/or subsurface particles smaller than 125 nm, such as smaller than 100 nm, including smaller than 80 nm, and further including smaller than 10 nm in their smallest dimension. Detecting and/or mapping surface and/or subsurface particles down to the level of 10 nm in height is important for hard disks of hard disk drives, as particles greater than 10 nm in height (e.g., from the surface) may corrupt the spacing between the hard disk and the read-write head of a hard disk drive. In some embodiments, for example, the apparatus may be configured for detecting and/or mapping surface and/or subsurface particles as small as or smaller than 4 nm in height.

The apparatus may be configured for detecting and/or mapping foreign surface features of articles, including surface and/or subsurface defects comprising scratches (e.g., circumferential scratches) that are micrometer-sized (i.e., admits of µm units as measured) or smaller, such as nanometer-sized (i.e., admits of nm units as measured) or smaller, such as angstrom-sized (i.e., admits of Å units as measured) or smaller, in their smallest dimension (e.g., length, width, or depth). With respect to micrometer-sized scratches, the apparatus may be configured for detecting and/or mapping scratches from, for example, 1 µm to 1000 µm in length, which may be significantly longer than the wavelength of photons emitted from a photon emitter of the apparatus. In some embodiments, for example, the apparatus may be configured for detecting and/or mapping scratches smaller than 1000 µm, such as smaller than 500 µm, including smaller than 250 µm, further including smaller than 100 µm, and even further including smaller than 50 µm in scratch length. With respect to nanometer-sized scratches, the apparatus may be configured for detecting and/or mapping scratches from, for example, 1 nm to 500 nm in scratch width. In some embodiments, for example, the apparatus may be configured for detecting and/or mapping scratches smaller than 500 nm, such as smaller than 250 nm, including smaller than 100 nm, further including smaller than 50 nm, and even further including smaller than 15 nm in scratch width. Surprisingly, due to a high level of spatial coherence, the apparatus may be configured for detecting and/or mapping angstrom-sized scratches with respect to scratch depth. In some embodiments, for example, the apparatus may be configured for detecting and/or mapping scratches smaller than 50 Å, such as smaller than 25 Å, including smaller than 10 Å, further including smaller than 5 Å, and even further including smaller than 1 Å (e.g., 0.5 Å) in scratch depth. For example, the apparatus may be configured for detecting and/or mapping scratches smaller than 500 µm in length, smaller than 100 nm in width, and smaller than 50 Å in depth.

The apparatus may be operable to accurately and/or precisely map or otherwise determine the position of a feature on an article's surface (e.g., FIGS. 6A (top) and 6B (top)). With respect to accuracy, the apparatus may be operable to map or otherwise determine the position of a feature on an article's surface within a micrometer-sized (i.e., admits of µm units as measured) radius or better. In some embodiments, for example, the apparatus may be operable to accurately map or otherwise determine the position of a feature on an article's surface within a radius of 100 µm, 90 µm, 80 µm, 70 µm, 60 µm, 50 µm, 40 µm, 30 µm, 20 µm, 10 µm, 9 µm, 8 µm, 7 µm, 6 µm, 5 µm, 4 µm, 3 µm, 2 µm, or 1 µm, or better. Combinations of the foregoing may also be used to describe the accuracy with which the apparatus may map or otherwise determine the position of a feature on an article's surface. In some embodiments, for example, the apparatus may be operable to accurately map or otherwise determine the position of a feature on an article's surface within a radius ranging from 1 µm to 100 µm, such as from 1 µm to 50 µm, including from 1 µm to 30 µm, and further including from 5 µm to 10 µm.

In addition to accurately and/or precisely mapping or otherwise determining the position of a feature on a surface of an article, the apparatus may be operable to accurately and/or precisely determine the photon scattering intensity distribution (e.g., FIGS. 6A (bottom) and 6B (bottom)) of the feature on the surface of the article. Such a photon scattering intensity distribution may be used characterize a surface feature of an article both quantitatively and qualitatively.

With respect to quantitative characterization of a surface feature of an article, mathematical integration of a photon scattering intensity distribution provides the size (e.g., volume) of the surface feature of the article. Quantitative characterization of a surface feature of an article may further include a determination of surface feature position on the article as described herein. Quantitative characterization may even further include the total number of surface features per article, or the number of surface features per unit area per article, as well as the number of each type of surface feature on the article. Such characterization information may be cataloged across a plurality of articles and be used to correct manufacturing trends should such features include surface and/or subsurface defects that might degrade the performance of the article.

With respect to qualitative characterization of a surface feature of an article, qualitative characterization may include a determination of the type of surface feature (e.g., particle, stain, scratch, void, etc.) of the article, which determination may be effected by, but is not limited to, analysis of photon scattering intensity distributions. Qualitative characterization may further include distinguishing between surface features known to differentially scatter photons with respect to wavelength; a polarization filter may be used to distinguish between surface features known to differentially scatter photons with respect to polarization; a coherence filter may be used to distinguish between surface features known to differentially scatter photons with respect to coherence; and a phase filter or waveplate may be used to distinguish between surface features known to differentially scatter photons with respect to phase. In some embodiments, for example, qualitative characterization of one or more surface features of an article may comprise contrasting photon-scattering information in the effective absence of one of the foregoing filters with photon-scattering information using one or more of the foregoing filters or contrasting a first surface features map produced in the effective absence of one of the foregoing filters with a second surface features map (or a plurality of surface features maps) produced using one or more of the foregoing filters. Along with quantitative characterization information, such qualitative characterization information may be cataloged across a plurality of articles and be used to correct manufacturing trends should such features include surface and/or subsurface defects that might degrade the performance of the article.

The apparatus described herein may be configured to process or inspect articles at a rate greater than or commensurate with the rate at which the articles or workpieces thereof are produced. In some embodiments, for example, the apparatus may be configured to process or inspect articles at a rate of at least 1, 2, 3, 4, 5, 6, 7, 8, 9, 10, 12, 14, 16, 18, or 20, or higher, article(s) per second, which rate may be commensurate with the rate at which the articles or workpieces thereof are produced. In some embodiments, for example, the apparatus may be configured to process or inspect articles at a rate of no more than 20, 18, 16, 14, 12, 10, 9, 8, 7, 6, 5, 4, 3, 2, or 1 article(s) per second, which rate may be commensurate with the rate at which the articles or workpieces thereof are produced. Combinations of the foregoing may also be used to describe the rate at which the articles or workpieces thereof are processed or inspected by the apparatus. In some embodiments, for example, the apparatus may be configured to process or inspect at least 1 and no more than 20 articles per second (e.g., between 1 and 20 articles per second), such as at least 1 and no more than 10 articles per second (e.g., between 1 and 10 articles per second), including at least 1 and no more than 5 articles per second (e.g., between 1 and 5 articles per second). Processing or inspecting articles at rates greater than or commensurate with the rate at which the articles or workpieces thereof are produced is a function of many features of the apparatus described herein, including, but not limited to, photon emitters and/or articles that need not be moved (e.g., for scanning) during processing or inspecting. For example, an article such as a hard disk of a hard disk drive need not be rotated during processing or inspecting. As such, the apparatus may be configured to hold an article stationary while emitting photons onto the surface of the article.

The apparatus described herein may be fully automated and function in different modes, including, but not limited to, an ultrafast mode, an ultrasensitive mode, and ultrasensitive plus mode. With respect to the ultrafast mode, the apparatus may operate at least 200 times faster than other optical surface analyzers (e.g., KLA-Tencor Candela CS10 or CS20), detect surface features such as defects comprising particles down to at least 100 nm, partially detect surface features such as defects comprising scratches (e.g., nanometer-sized scratches), and provide measurements of roughness. With respect to the ultrasensitive mode, the apparatus may operate at least 50 times faster than other optical surface analyzers, detect surface features such as defects comprising particles down to at least 30 nm, and provide measurements of roughness. With respect to the ultrasensitive plus mode, the apparatus may operate at least 20 times faster than other optical surface analyzers, detect surface features such as defects comprising particles down to at least 30 nm, fully detect surface features such as defects comprising scratches (e.g., nano-scratches), and provide measurements of roughness.

As such, provided herein is an apparatus, comprising a photon emitter configured for emitting photons onto a surface of an article; a combination of reflective surfaces comprising a first reflective surface and a second reflective surface, wherein the combination of reflective surfaces is configured for reflecting photons onto the surface of the article; a photon detector array configured for detecting photons scattered from surface features of the article; and a processing means configured for processing photon-detector-array signals corresponding to photons scattered from the surface features of the article. In some embodiments, the combination of reflective surfaces is operable to increase the photon flux at the surface of the article by at least a factor of two over the photon flux at the surface of the article provided by the photon emitter in the absence of the combination of reflective surfaces. In some embodiments, the combination of reflective surfaces is operable to increase the photon flux at the photon detector array by at least a factor of three over the photon flux at the photon detector array in the absence of the combination of reflective surfaces. In some embodiments, the first reflective surface comprises a one-way mirror and photons pass through the one-way mirror onto the surface of the article. In some embodiments, the second reflective surface comprises a mirror and photons reflect from the mirror back onto the surface of the article. In some embodiments, the apparatus further comprises a third reflective surface of the combination of reflective surfaces, wherein the third reflective surface comprises the surface of the article. In some embodiments, the apparatus further comprises a third reflective surface of the combination of reflective surfaces, wherein the article is transparent, and wherein the article is positioned parallelly proximate to the third reflective surface. In some embodiments, the apparatus further comprises a telecentric lens coupled to the photon detector array. In some embodiments, the processing means comprises one or more computers or equivalent devices configured for mapping the surface features of the article.

Also provided is an apparatus, comprising a photon emitter configured for emitting photons onto a surface of an article; a first reflective surface and a second reflective surface configured to reflect the photons onto the surface of the article; and a processing means configured for processing signals from a photon detector array corresponding to photons scattered from surface features of the article. In some embodiments, the first reflective surface and the second reflective surface are operable to increase the photon flux at the surface of the article by at least a factor of two over the photon flux at the surface of the article provided by the photon emitter in the absence of the first reflective surface and the second reflective surface, and the first reflective surface and the second reflective surface are operable to increase the photon flux at the photon detector array by at least a factor of three over the photon flux at the photon detector array in the absence of the first reflective surface and the second reflective surface. In some embodiments, the first reflective surface is a one-way mirror and photons pass through the one-way mirror onto the surface of the article, and the second reflective surface is a mirror. In some embodiments, the apparatus further comprises a third reflective surface, wherein the third reflective surface comprises the surface of the article. In some embodiments, the apparatus further comprises a third reflective surface, wherein the article is transparent, and wherein the article is positioned parallelly proximate to the third reflective surface. In some embodiments, the processing means comprises one or more computers or equivalent devices configured for mapping the surface features of the article.

Also provided is an apparatus, comprising a photon emitter configured for emitting photons onto a surface of an article; a combination of reflective surfaces comprising a first reflective surface and a second reflective surface, wherein the combination of reflective surfaces is configured for reflecting photons onto the surface of the article; a lens-and-photon-detector-array combination configured for collecting and detecting photons scattered from surface features of the article, wherein the lens is a telecentric lens; and a processing means configured for processing photon-detector-array signals corresponding to photons scattered from the surface features of the article. In some embodiments, the combination of reflective surfaces is operable to increase the photon flux at the surface of the article by at least a factor of two over the photon flux at the surface of the article provided by the photon emitter in the absence of the combination of reflective surfaces, and the combination of reflective surfaces is operable to increase the photon flux at the photon detector array by at least a factor of three over the photon flux at the photon detector array in the absence of the combination of reflective surfaces. In some embodiments, the first reflective surface is a one-way mirror and photons pass through the one-way mirror onto the surface of the article, and the second reflective surface is a mirror and photons reflect from the mirror back onto the surface of the article. In some embodiments, the apparatus further comprises a third reflective surface of the combination of reflective surfaces, wherein the third reflective surface comprises the surface of the article. In some embodiments, the apparatus further comprises a third reflective surface of the combination of reflective surfaces, wherein the article is transparent, and wherein the article is positioned parallelly proximate to the third reflective surface. In some embodiments, the processing means comprises one or more computers or equivalent devices configured for mapping the surface features of the article.

Also provided is an apparatus, comprising a combination of reflective surfaces comprising a first reflective surface and a second reflective surface, wherein the combination of reflective surfaces is configured for reflecting photons onto a surface of an article; a photon detector array configured for detecting photons scattered from surface features of the article; and a processing means configured for processing photon-detector-array signals corresponding to photons scattered from the surface features of the article. In some embodiments, the combination of reflective surfaces is operable to increase the photon flux at the surface of the article by at least a factor of two over the photon flux at the surface of the article provided by a photon emitter in the absence of the combination of reflective surfaces, and the combination of reflective surfaces is operable to increase the photon flux at the photon detector array by at least a factor of three over the photon flux at the photon detector array in the absence of the combination of reflective surfaces. In some embodiments, the first reflective surface comprises a one-way mirror and photons pass through the one-way mirror onto the surface of the article, the second reflective surface comprises a mirror and photons reflect from the mirror back onto the surface of the article, and the apparatus further comprises a third reflective surface of the combination of reflective surfaces comprising the surface of the article. In some embodiments, the first reflective surface comprises a one-way mirror and photons pass through the one-way mirror onto the surface of the article, the second reflective surface comprises a mirror and photons reflect from the mirror back onto the surface of the article, and the apparatus further comprises a third reflective surface of the combination of reflective surfaces comprising a mirror positioned parallelly proximate to a transparent article. In some embodiments, the processing means comprises one or more computers or equivalent devices configured for mapping the surface features of the article.

While some particular embodiments have been described and/or illustrated herein, and while these particular embodiments have been described and/or illustrated in considerable detail, it is not the intention of the applicant(s) for these particular embodiments to limit the concepts presented herein. Additional adaptations and/or modifications may readily appear to persons having ordinary skill in the art, and, in broader aspects, these adaptations and/or modifications may be encompassed as well. Accordingly, departures may be made from the foregoing embodiments without departing from the scope of the concepts presented herein, which scope is limited only by the following claims when appropriately construed.

What is claimed is:

1. An apparatus, comprising:
a photon emitter configured for emitting photons onto a surface of an article;
a flash lamp configured to minimize vibrations while detecting photons scattered from features in the surface of the article;
a combination of reflective surfaces comprising a first reflective surface and a second reflective surface,
wherein the first reflective surface and the second reflective surface are each configured for reflecting photons reflected from the surface of the article back onto the surface of the article;
a photon detector array configured for detecting photons scattered from surface features of the article; and
a computing device configured for processing photon detector array signals corresponding to photons scattered from the surface features of the article.

2. The apparatus of claim 1, wherein the combination of reflective surfaces is operable to increase photon flux at the surface of the article by at least a factor of two over the photon flux at the surface of the article provided by the photon emitter in the absence of the combination of reflective surfaces.

3. The apparatus of claim 1, wherein the combination of reflective surfaces is operable to increase photon flux at the photon detector array by at least a factor of three over the photon flux at the photon detector array in the absence of the combination of reflective surfaces.

4. The apparatus of claim 1, wherein the first reflective surface comprises a one-way mirror configured to pass photons through the one-way mirror onto the surface of the article.

5. The apparatus of claim 1, wherein the second reflective surface comprises a mirror configured to reflect photons reflected from the mirror back onto the surface of the article.

6. The apparatus of claim 1, further comprising a third reflective surface of the combination of reflective surfaces, wherein the third reflective surface comprises the surface of the article.

7. The apparatus of claim 1, further comprising a third reflective surface of the combination of reflective surfaces, wherein the article is transparent, and wherein the article is positioned parallelly proximate to the third reflective surface.

8. The apparatus of claim 1, further comprising a telecentric lens coupled to the photon detector array.

9. The apparatus of claim 1, wherein the computing device is further configured for mapping the surface features of the article.

10. An apparatus, comprising:
a photon emitter configured for emitting photons onto a surface of an article,
wherein the photon emitters comprise a flash lamp configured to minimize vibrations while detecting photons scattered from features in the surface of the article;
a first reflective surface and a second reflective surface that are each configured to reflect photons reflected from the surface of the article back onto the surface of the article; and
a computing device configured for processing signals from a photon detector array corresponding to photons scattered from surface features of the article.

11. The apparatus of claim 10, wherein the first reflective surface and the second reflective surface are operable to increase photon flux at the surface of the article by at least a factor of two over the photon flux at the surface of the article provided by the photon emitter in the absence of the first reflective surface and the second reflective surface, and wherein the first reflective surface and the second reflective surface are operable to increase the photon flux at the photon detector array by at least a factor of three over the photon flux at the photon detector array in the absence of the first reflective surface and the second reflective surface.

12. The apparatus of claim 10, wherein the first reflective surface is a one-way mirror and photons pass through the one-way mirror onto the surface of the article, and wherein the second reflective surface is a mirror.

13. The apparatus of claim 10, further comprising a third reflective surface, wherein the third reflective surface comprises the surface of the article.

14. The apparatus of claim 10, further comprising a third reflective surface, wherein the article is transparent, and wherein the article is positioned parallelly proximate to the third reflective surface.

15. The apparatus of claim 10, wherein the computing device is further configured for mapping the surface features of the article.

16. An apparatus, comprising:
   a combination of reflective surfaces comprising a first reflective surface and a second reflective surface, wherein the first reflective surface and the second reflective surface area each configured for reflecting photons reflected from a surface of an article back onto the surface of the article;
   a photon detector array configured for detecting photons scattered from surface features of the article;
   a flash lamp for minimizing vibrations while detecting photons scattered from features in the surface of the article; and
   a computing device configured for processing photon detector array signals corresponding to photons scattered from the surface features of the article.

17. The apparatus of claim 16, wherein the combination of reflective surfaces is operable to increase photon flux at the surface of the article by at least a factor of two over the photon flux at the surface of the article provided by a photon emitter in the absence of the combination of reflective surfaces, and wherein the combination of reflective surfaces is operable to increase the photon flux at the photon detector array by at least a factor of three over the photon flux at the photon detector array in the absence of the combination of reflective surfaces.

18. The apparatus of claim 16, wherein the first reflective surface comprises a one-way mirror configured to pass photons through the one-way mirror onto the surface of the article, wherein the second reflective surface comprises a mirror configured to reflect photons from the mirror back onto the surface of the article, and the apparatus further comprises a third reflective surface of the combination of reflective surfaces, wherein the third reflective surface comprises the surface of the article.

19. The apparatus of claim 16, wherein the first reflective surface comprises a one-way mirror configured to pass photons through the one-way mirror onto the surface of the article, wherein the second reflective surface comprises a mirror configured to reflect photons from the mirror back onto the surface of the article, and the apparatus further comprises a third reflective surface of the combination of reflective surfaces, wherein the article is transparent, wherein the third reflective surface comprises a mirror positioned parallelly proximate to the article.

20. The apparatus of claim 16, wherein the computing device is further configured for mapping the surface features of the article.

* * * * *